(12) United States Patent
Keren

(10) Patent No.: US 7,591,791 B2
(45) Date of Patent: Sep. 22, 2009

(54) DIAGNOSTIC THIMBLE

(75) Inventor: Tomer Keren, Rishon Le Zion (IL)

(73) Assignee: Inverness Medical Switzerland GmbH, Zug (CH)

( * ) Notice: Subject to any disclaimer, the term of this patent is extended or adjusted under 35 U.S.C. 154(b) by 0 days.

(21) Appl. No.: 11/766,203

(22) Filed: Jun. 21, 2007

(65) Prior Publication Data

US 2008/0319347 A1    Dec. 25, 2008

(51) Int. Cl.
*A61B 5/00*     (2006.01)
*B65D 81/00*    (2006.01)
*C12M 1/34*     (2006.01)
*C12M 3/00*     (2006.01)

(52) U.S. Cl. .................... 600/584; 435/287.1
(58) Field of Classification Search ............... 600/300, 600/301, 309, 500, 509, 583, 584; 128/920; 422/100, 101, 55–58, 61, 68.1; 435/7.1, 435/286.4, 287.1, 287.2, 287.9; 606/181–183
See application file for complete search history.

(56) References Cited

U.S. PATENT DOCUMENTS

| | | | |
|---|---|---|---|
| 6,555,390 B2 * | 4/2003 | Chandler | 436/518 |
| 6,617,116 B2 * | 9/2003 | Guan et al. | 435/7.1 |
| 7,279,136 B2 * | 10/2007 | Takeuchi et al. | 422/100 |
| 2005/0159678 A1 * | 7/2005 | Taniike et al. | 600/583 |
| 2007/0100213 A1 * | 5/2007 | Dossas et al. | 600/300 |

FOREIGN PATENT DOCUMENTS

GB    2090659 A   *   7/1982
JP    09266889 A  *   10/1997

* cited by examiner

*Primary Examiner*—Max Hindenburg
*Assistant Examiner*—Brian Szmal
(74) *Attorney, Agent, or Firm*—Sheppard, Mullin, Richter & Hampton LLP

(57) ABSTRACT

A diagnostic device for performing a diagnostic blood test of a subject comprising a thimble-like element adapted to be engaged with the subject's finger, a puncturing unit for producing a blood sample from the subject's finger, and an at least one test element in flow communication with said blood sample.

19 Claims, 5 Drawing Sheets

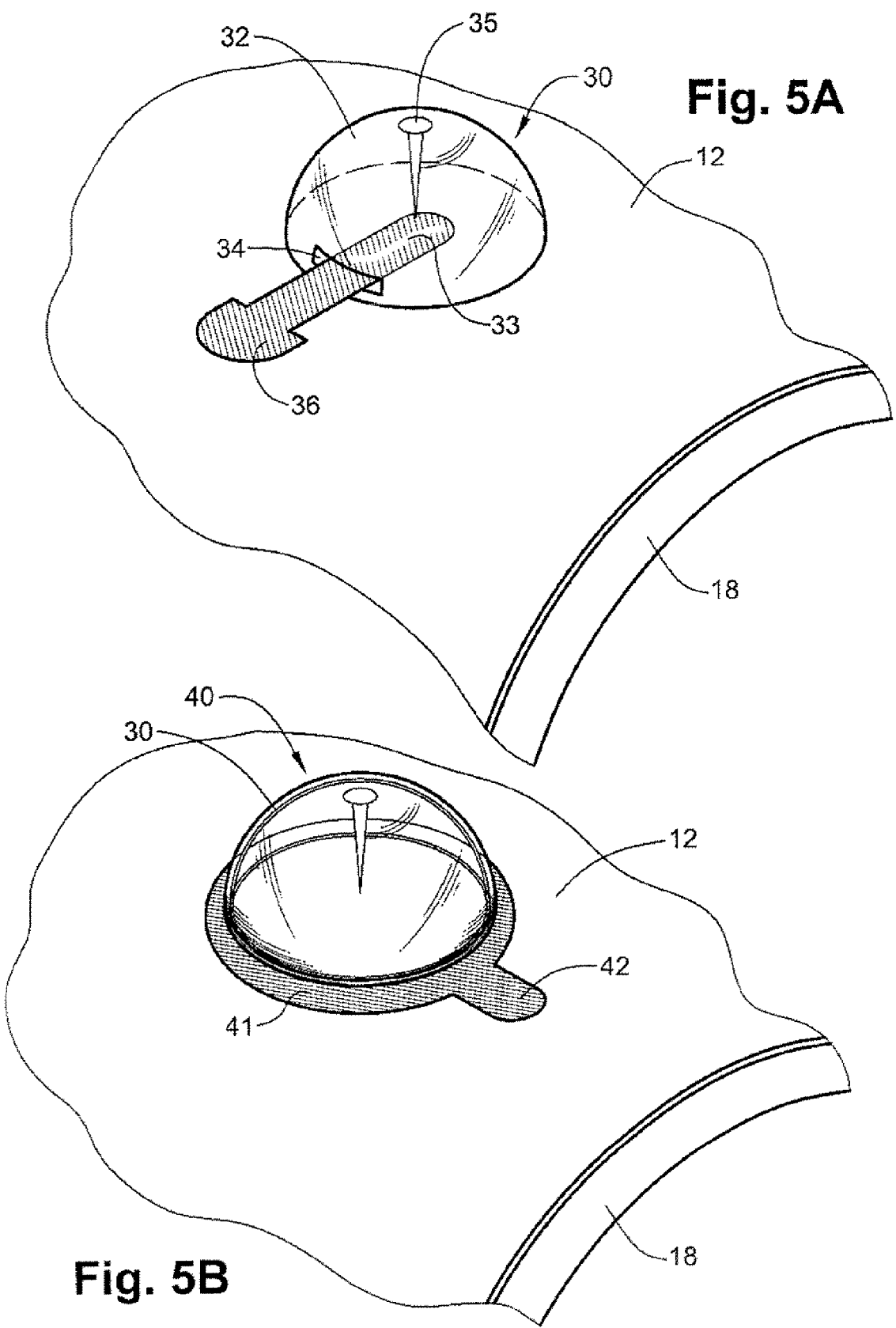

DIAGNOSTIC THIMBLE

BACKGROUND OF THE INVENTION

1. Field of the Invention

The present invention generally relates to medical diagnostics devices and more specifically to a diagnostic thimble mountable on a subject's finger for performing a rapid blood test.

2. Discussion of the Related Art

Diagnostics test kits for rapid detection of specific medical conditions and diseases are becoming increasingly widespread in the field of medical diagnosis. Such kits allow for immediate point-of-care diagnosis in the most basic of healthcare settings with no need for expensive instrumentation and with minimal specialized training.

A well-known format for performing rapid assays is the lateral flow platform where a sample is applied to a test strip impregnated with assay specific reagents, typically a binding assay such as immunoassay. The sample is applied to one end of the test strip and is drawn through the strip by capillary action to pass through a reaction zone where the analyte, when present, reacts with the pre-impregnated reagents and further into a detection zone where the appearance of a visible or otherwise detectable signal indicates presence of the analyte in the sample. There exist many variations of this basic structure, regarding the number and nature of the immobilized, labeling and other reagents located along the strip and their interaction with the analyte as well as to the nature and formation of the signal. A great variety of analytes may be detected in this manner. In particular relevant to the present invention are rapid diagnostic blood tests where the presence of a specific substance in the blood is indicative of the presence or absence of a disease or a physiological condition, such as for example, the Determine® series from Inverness Medical for the detection of sexually transmitted diseases, including HIV, Hepatitis B and Syphilis.

Although available rapid blood testing kits, such as the Determine® series, significantly shorten and simplify blood test procedures, they still require separate actions for collecting a blood sample from a tested subject and transferring the sample to the test device for analysis. Collection of blood sample visually involved withdrawing blood by means of a syringe needle or the use of a lancet to injure a body area such as a fingertip and collecting blood from the injury by means of a capillary tube. Such procedures are typically performed by a trained person and may expose the person to infectious blood samples. Moreover, blood sample collection and sample testing are not necessarily performed by the same person. Often blood specimens are collected in one location while tests are performed in another location. This requires transporting the collected specimens and a double identification recordation first for labeling the collected blood samples and then for labeling the test devices, e.g., test strips. In particular, where large groups of people are to be screened for an infectious agent, such as for example HIV, and where it is possible that tested individuals will not come for follow-up, it is particularly desirable to have means for obtaining rapid results while providing easy identification means that prevents possible mismatch between test subjects and test results. Additionally, some people and in particular children are intimidated by the sight of a needle or a lancet or by the sight of blood and consequently may not cooperate with the medical personnel who are trying to take a sample of their blood. In such cases it is desirable to conceal the sight of the lancing element from the tested subject and to perform the act of injury as fast as possible.

It will be therefore desirable to have an all-in-one self-contained diagnostic device, which allows performing both collection and subsequent analysis of a blood sample in the same device with no need to transfer the collected sample to a separate test device. Such a device will simplify test procedure, will reduce the time required for the test and will minimize exposure of personnel to collected blood samples. It will be also desirable to have such an all-in-one blood test device which can be mounted on a subject finger before the test is started and which can be activated with minimum awareness of the subject to the act of injury. Such a device will further eliminates the need to manage separate identification labels for blood samples and for test devices and will prevent possible mismatch between tested subjects and test results.

SUMMARY OF THE PRESENT INVENTION

It is a general object of the present invention to provide an all-in-one self-contained rapid diagnostic device for performing both collection and analysis of a blood sample of a test subject by a one-step operation with no need to manipulate blood samples.

It is a further object of the invention to provide such a diagnostic device as defined above which is configured as a thimble to be placed over the end of the subject's finger and to optionally remain attached to the finger until the test is complete and test results are visibly displayed.

Such a device has the advantages of simplifying test procedure and minimizing exposure of health care practitioners to blood samples and to lancing devices. It has the further advantage of eliminating the need to manage separate identification records of blood samples and test devices.

Accordingly the present invention provides a diagnostic device engagabale with a subject's finger for a rapid detection of a pre-selected analyte in the subject's blood. The analyte may be a blood borne pathogen or any other substance the presence of which is indicative of a disease or a physiological condition.

The diagnostic device of the invention comprises a thimble-like element adapted to be engaged with the subject's finger, a puncturing unit for producing a blood sample from the subject's finger, and an at least one test element accommodated inside the thimble-like element in a flow communication with the blood sample. The diagnostic device further comprises a display window through which test results can be visibly read. The puncturing unit may comprise a lancing element mounted within a flexible housing or any other lancet unit with an automatic retraction mechanism. The thimble-like element comprises a hollow cylindrical member including a transparent window for viewing the test results.

The test element is preferably a diagnostic strip adapted for a lateral flow assay of a whole blood sample wherein the assay may be an immunoassay an enzymatic assay, a biochemical assay or a chemical assay. Preferably said assay is a positive/negative assay for detecting the presence of an analyte in the blood sample. Yet, according to other embodiments, the assay may be a quantitative or a semi-quantitative assay for detecting the concentration of the analyte. In accordance with a certain embodiment of the invention the analyte is a blood born pathogen. Preferably the diagnostic strip comprises a sample receiving zone, a whole blood separation zone for entrapping and retaining red blood cells, a reaction zone and a detection zone.

Optionally the device further includes a reservoir of a releasable reagent solution adapted to release the reagent solution to facilitate running the diagnostic test. The reservoir may comprise a blister made of liquid impermeable film for encapsulating the reagent solution. Optionally the device may further comprise a safety means for preventing premature activation of the puncturing units.

BRIEF DESCRIPTION OF THE DRAWINGS

The present invention will be understood and appreciated more fully from the following detailed description taken in conjunction with the drawings in which:

FIGS. 5A and 5B illustrate two embodiments of a puncturing unit with a safety means for preventing premature puncturing;

DETAILED DESCRIPTION OF THE PREFERRED EMBODIMENT

The present invention provides a thimble-like all-in-one self-contained blood-test diagnostic device for a rapid detection of a pre-selected analyte in a blood sample. The device allows for performing a blood test by one operation step with no need to handle or manipulate blood samples, thus preventing exposure of health care providers to blood samples. The device has the further advantage of reducing to zero the time lag between initial sample collection and test performing.

The device of the invention is configured as a thimble that is easily placed over the end of a finger. The term thimble refers to a device which at least partially covers a finger, having a general geometry of a hollow cylinder such as a sleeve, with one open for receiving a finger. The device includes a puncturing unit with a self retracting mechanism for producing a blood sample, at least one test element in flow communication with the sample blood so produced and a display window for viewing the test results. The test element may be any test element known in the art for rapid detection of an analyte in a whole blood sample. Preferably the test element is a lateral flow diagnostic strip configured for displaying test results within less than 30 minutes, more preferably within 5 to 15 minutes, by a clearly interpreted visible signal with no need for further equipment for interpretation. By selecting a suitable test element, the diagnostic thimble of the invention may be used to detect various diseases and medical conditions. For example, the device may be used for a rapid detection of infectious diseases such as HIV and hepatitis or for diagnosing myocardial infarction by monitoring cardiac markers. The device is especially useful for testing individuals for example young children, who fail to cooperate during blood tests. The device also allows for screening a large number of subjects in a simple straightforward manner with no need to manage separate labeling for samples and for test devices. The device may be used in developing areas where it is necessary to screen population for infectious diseases or for screening admitted patients in emergency rooms. The device may also be used at blood donation sites for screening potential donors.

Figure 1:
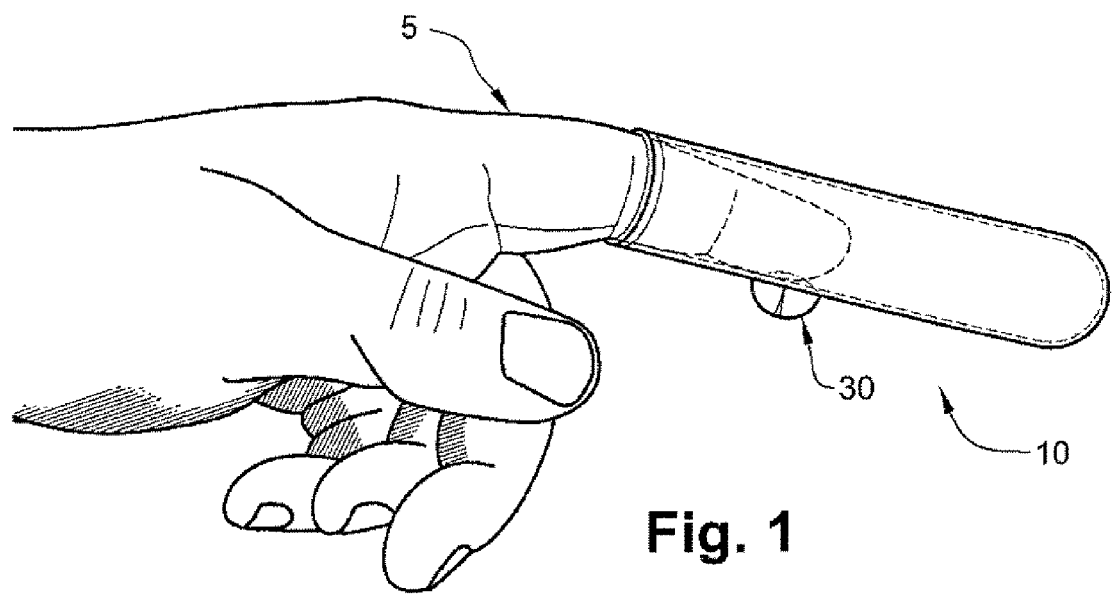
FIG. 1 illustrates a diagnostic thimble of the present invention placed over a finger of a test subject.
Figure 2:
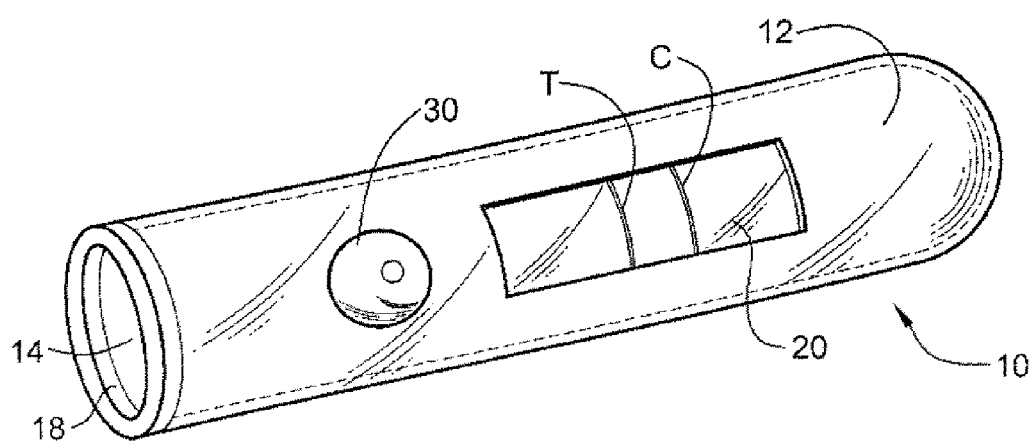
FIG. 2 is an isometric view of the diagnostic thimble of the invention.
Figure 3:
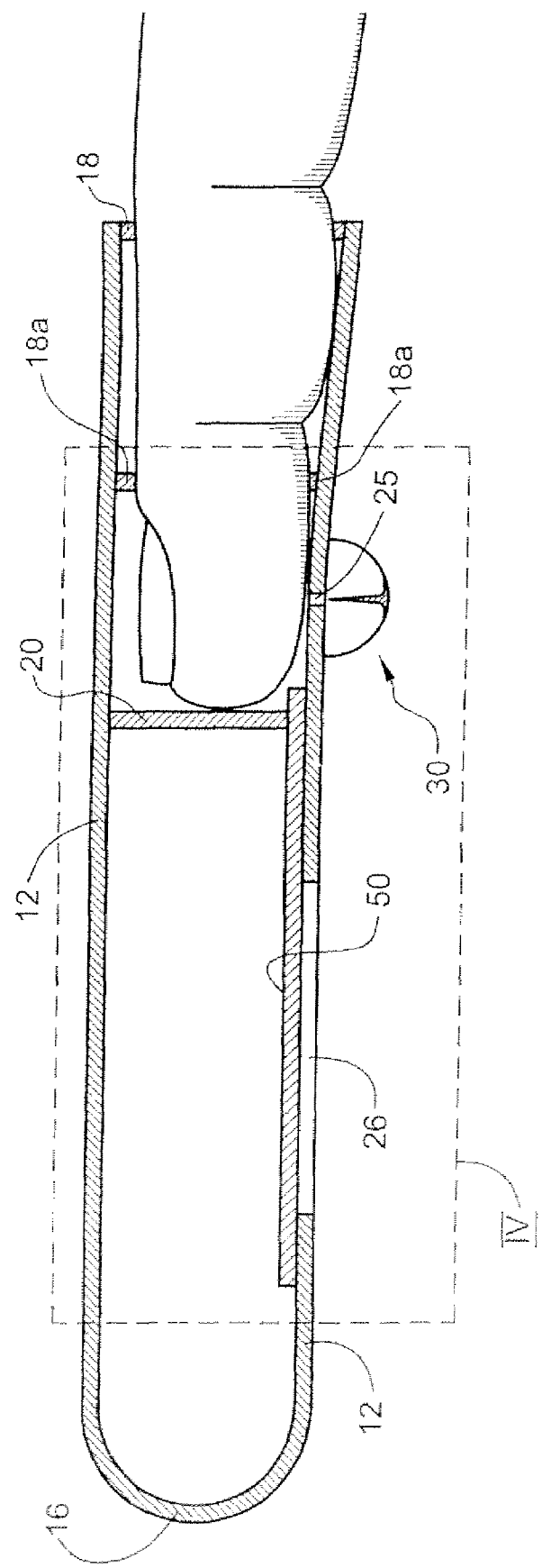
FIG. 3 is a cross sectional side view of the thimble placed over a subject's finger.

Turning now to the drawings, where like numerals refer to like elements, there is shown a diagnostic thimble, generally designated 10, in accordance with a preferred embodiment of the present invention. Device 10 comprises a thimble body 12 of a cylindrical shape, a self return puncturing unit 30 and a diagnostic strip 50 mounted within thimble body 12. Thimble body 12 is open at one end 14 for receiving a finger 5 and is preferably closed at the opposite end 16. Thimble body 12 can be fabricated from any rigid material. Preferably body 12 is fabricated from low-cost sterilizable plastic material such as PET (polyethylene), polystyrene and the like by a mold injection process. Body 12 is provided with a clear transparent window 26 through which test results are visibly displayed. The rest of body 12 may be made transparent, translucent or opaque. In accordance with one embodiment body 12 is made opaque to obscure the sight of the lancing element and of the blood when the test is carried on. Puncturing unit 30, comprising a lancing element 35, is accessible from the external surface of body 12 and is provided with a self return mechanism. Device 10 may be fabricated in a variety of sizes to fit persons of various sizes. As best seen in FIG. 3, when in use, thimble body 12 is placed over the end of finger 5 such that piercing unit 30 is located opposite the soft tissue of finger pillow 4 where there is a high density of small blood vessels. A stopper wall 20 located at a predetermined distance from opening 14 adjusts the position of finger 5 in relation to puncturing unit 30 by preventing the finger from penetrating further into the body cavity. An elastic annular rubber flange 18 may also be provided near opening 14 to enhance the gripping of device 10 on the finger and to keep it in place. It will be realized that flange 18 is not necessarily located at opening 14 but may be located further inside cylindrical body 12 between opening 14 and puncturing unit 30. To further enhance gripping of the thimble and to prevent its movement or removal during the test, an adhesive medical tape (not shown) may be wrapped around end 14 and the finger.

Figure 4:
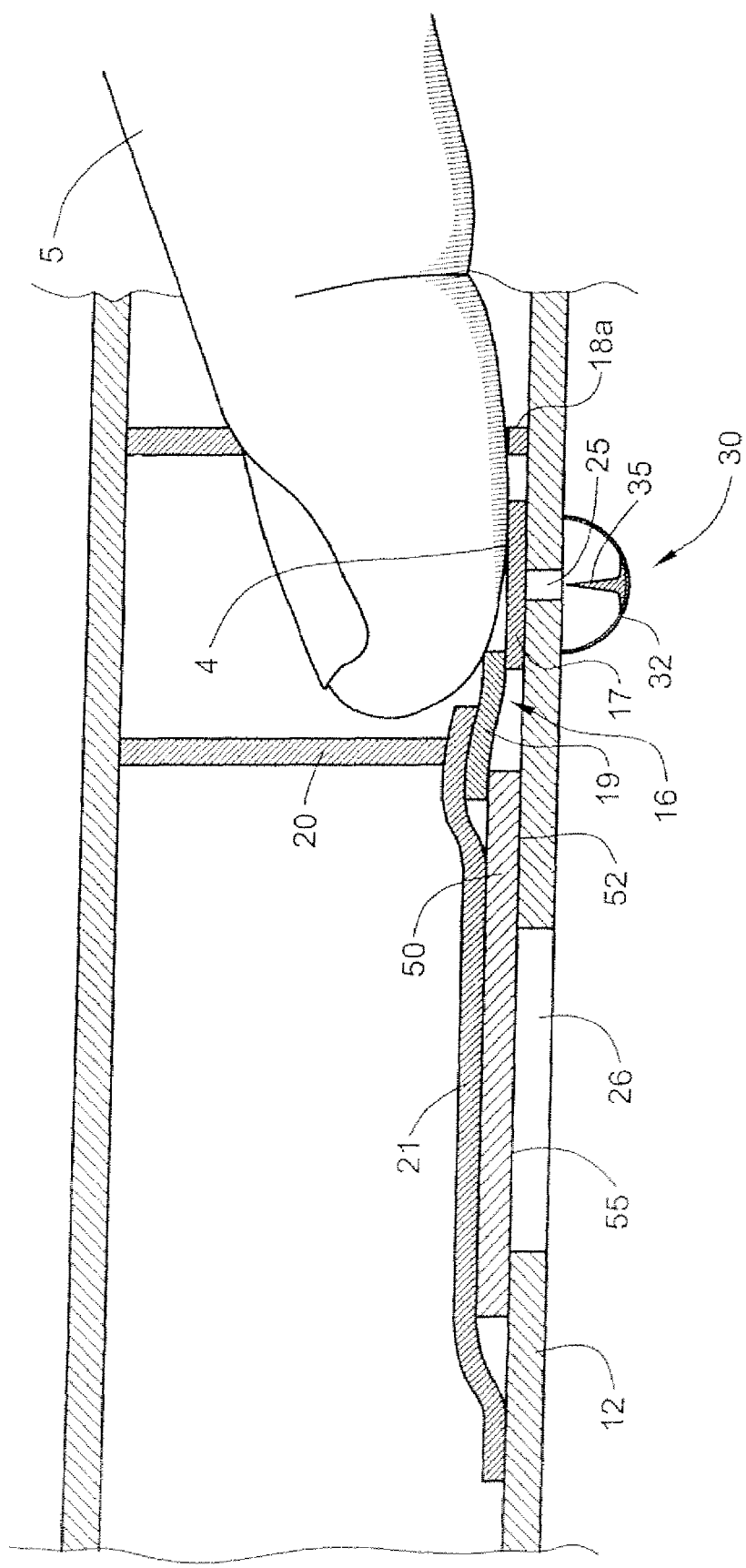
FIG. 4 is an exploded partial longitudinal cross sectional view of the diagnostic thimble in the area designated by the broken lines of FIG. 3.

A small opening 25 in wall 12 allows lancet 35 when fired to penetrate through wall 12 into finger tip 4. Opening 25 is covered on the inner side of wall 12 by an elastomeric self-sealing liquid-impermeable membrane so that the hole formed by lancet 35 will immediately close on itself after the lancet is withdrawn, preventing blood from escaping through opening 25. Test strip 50 is located downstream of opening 25 in direct contact with wall 12. The detection zone 55 of strip 50 is placed over transparent window 26. The sample receiving zone 52 of strip 50 extends through a hermetically sealed slit in wall 20 to the other side of the wall toward the puncturing site. When finger 5 is pressed against wall 20, a cavity 16 is formed between the finger and walls 12 and 20 where blood is produced by lancet 35. A second flange 18a (only the bottom part of which is shown in FIG. 4) may optionally be provided near opening 25 to ensure that the blood would not flow toward opening 14. Alternatively, flanges 18 and 18a may be the same flange located close to the upstream side of opening 25. Thus, blood produced inside the cavity is drawn into the receiving zone of strip 50 and further downstream by capillary action into the detection zone of the strip. A wick member 19, having one end in contact with the inner surface of membrane 17 and a second end in contact with the sample receiving zone of strip 50 may optionally be added to serve as a bridging element between the two. Wick member 19 may be made of glass fiber, polyester or other filter material known in the art. Alternatively, sample receiving end 52 may be in direct contact with membrane 17 or may be positioned on top of membrane 17 directly below lancet 35 such that blood is directly applied on the sample receiving zone. For some applications, wick 52 as well as zone 52 may be impregnated with medically approved anticoagulants or bleeding enhancers, such as for example citrate and EDTA. A liquid impermeable film 21 laid over strip 50 and partially over wick 19 envelopes strip 50 between body 12 and film 52.

Figure 6A:
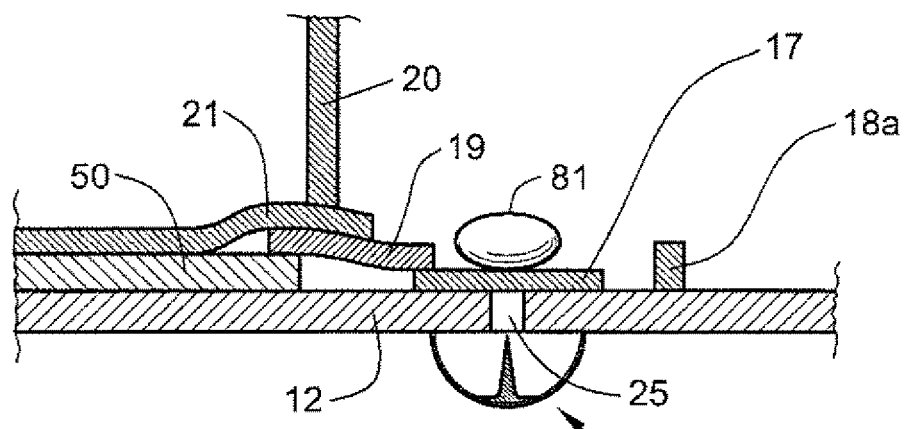
FIGS. 6A and 6B are partial cross sections of two configurations of the diagnostic thimble of the invention incorporating a reagent reservoir.
Figure 6B:
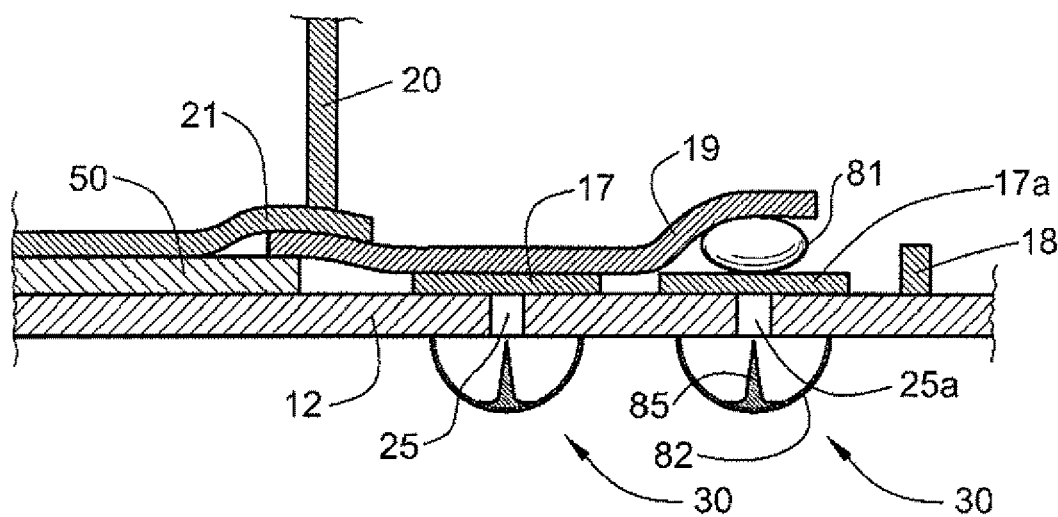

Puncturing unit 30, comprising a sterile lancing element 35, is configured for penetrating the skin of finger tip 4 for drawing blood. Lancing element 35 may be a hollow or a solid needle or any other sharp sterile element suitable for lancing dermal tissue for producing at least one drop of blood. The size and shape of lancing element 35 as well as the depth to which it penetrates the skin tissue may vary and designed in accordance with the amount of blood required for performing the test. In its default position, the tip of lancet 35 is pointing at opening 25 from outside body 12. Upon firing, lancing element 35 penetrates through opening 25 and membrane 17 into finger tip 4. Puncturing unit 30 is provided with automatic return/retract mechanism for withdrawing lancet 35 back to its default retracted position immediately after firing. Various mechanisms may be employed for the firing of unit 30. FIG. 6 depict an embodiment according to which lancing element 35 is fixedly mounted within an elastic or spring-loaded capsule-like housing 32. Puncturing unit 30 is fired by pressing housing 32 toward body 12 thereby lancet 35 penetrates through opening 25 into the finger. Upon release, housing 32 as well as the lancet bounce back to their default position. Alternatively, lancet 35 may be movably mounted within a rigid housing and provided with a spring mechanism that biases the lancet into its retracted position. Yet in accordance with other embodiments, the puncturing unit may be an available single-use skin pricking unit, such as For example a Unistik® unit available from Owen Mumford, mounted on body 12 and if necessary adjusted or modified to operate in association therewith. Preferably, unit 30 is further provided with a safely locking means for preventing unintentional premature actuation of the unit. FIGS. 6A and 6B depict two possible configurations of such a safety means. In accordance with the configuration shown in FIG. 6A, such a safety means is formed by a movable rigid plastic slip 33 that extends across opening 23 of unit 30 and is having an outward extension 36 extending out of housing 32 through opening 34. In its locking position slip 33 is placed beneath lancet 35 to block the lancet movement. Upon pulling slip 33, the lancer is ready for activation. A second safety mechanism is depicted in FIG. 6B according to which a removable rigid cap 40, attached to body 12 by means of adhesive rim 41, is placed on top of unit 30 protecting unit 30 from being activated. A pulling tab 42 provided extending from rim 41 allows the removal of protective cap 40 immediately before the test is to be performed.

The size and shape of lancing element 35 as well as the depth to which it penetrates the skin tissue may be designed in accordance with the amount of blood required for the specific diagnostic test strip embedded within the thimble. Typically, the amount of blood required for lateral flow assays is in the range of 5 to 100 µL. Such amounts can be easily obtained by means of piercing the top layers of the skin. However it is sometimes necessary to add a small amount of an additional reagent, usually a diluent fluid, such as a buffer solution, in order to perform the test. The buffer could be for example a phosphate buffered saline or Tris buffered saline. For this purpose, the diagnostic thimble of the invention may further include a small reservoir of medically approved buffer or other appropriate reagent solution, adapted to release its content at the same time, or at a predetermined time before or after, puncturing unit 30 is fired. FIGS. 6A and 6B illustrate two embodiments of the diagnostic thimble with an additional reagent reservoir 81. In accordance with the embodiment depicted in FIG. 6A, a blister 81 filled with the required amount of reagent solution, is positioned above membrane 17 in the path of lancet 35 such that when puncturing unit 30 is activated blister 81 is punctured to release its content. Blister 81 may be fabricated from any thin liquid impermeable membrane such as polyethylene, nylon or the like that is easily punctured by a sharp element. The amount of reagent in blister 81 is typically in the range of 20 to 100 µL, depending on the specific diagnostic test. FIG. 9B depicts another configuration according to which blister 81 is located in cavity 16 downstream of the puncturing site and upstream of strip 50. The device is provided with an additional puncturing unit 80, similar in design to puncturing unit 30 adapted for puncturing blister 81. In accordance with this embodiment, blister 81 is punctured either simultaneously or shortly before or after unit 30 is fired such that the reagent solution released from blister 81 is mixed with the blood as it flows into cavity 16 and further into strip 50.

Figure 7:
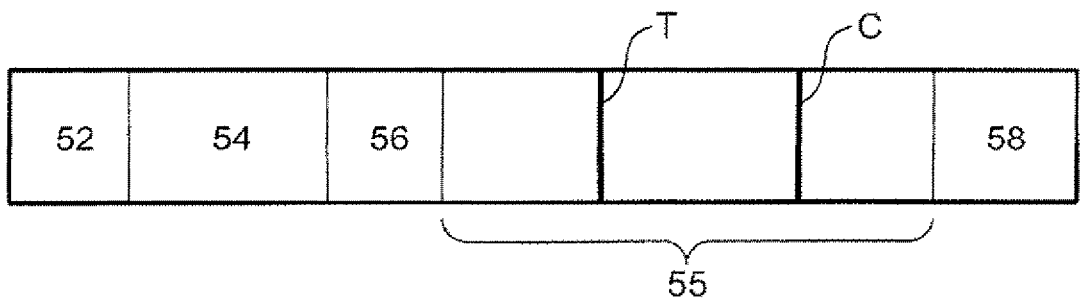
FIG. 7 illustrates a typical test strip suitable for use in the present invention.

Diagnostic strip 50 may be any diagnostic test strip known in the art for detecting an analyte in a whole blood sample by a lateral flow assay, including immunoassays, enzymatic assays, biochemical assays and chemical assays. FIG. 7 illustrates a typical test strip suitable for use in the present invention, comprising a sample receiving zone 52, a whole blood separation zone 54, a reaction zone 56, a detection zone 55 and an absorbent pad or wick 58 for receiving the fluid and promoting capillary flow through the strip. The different zones may be constructed from one or more bibulous or non-bibulous porous solid phase materials ordered sequentially in an abutting or partial overlapping manner to form a fluid communication therebetween. Strip 50 may be supported on a backing support and/or laminated between two impermeable non-absorbing films such as mylar films, at least one of which is transparent or translucent for allowing viewing the signal. The lateral flow assay is carried out by applying the sample at the sample receiving zone 52 and allowing it to travel along the strip by capillary action, to react with the reagents provided in zone 56 and further downstream to be captured and concentrated at the detection/capture zone 55. Sample receiving zone 52 is the area of a test strip 50 where the sample is applied. Sample receiving zone 52 can include a bibulous or non-bibulous material, such as filter paper, nitrocellulose, glass fibers, polyester or other appropriate materials. Zone 52 can also include compounds or molecules that may be necessary or desirable for optimal performance of the test, for example, buffers, stabilizers, surfactants and the like. Separation zone 54 is constructed from a material capable of separating the fluid portion of the whole blood sample from the red blood cells by entrapping and retaining the red blood cells therein while transporting the blood plasma or blood serum downstream along the strip so as not to obscure the detection zone 55 by the red color of the red-blood cells. Separation zone 54 may be made of a porous membrane that acts as a physical barrier for the red blood cells or m ay be treated with cell agglutinating reagent to facilitate the separation of the red blood cells from the blood fluid. Reaction or reagent zone 56 is where reagents useful in the detection of the analyte, such as a labeled specific binding member of a first specific binding pair, are bound either movably or immobilized. Typically, the analyte, when present, reacts with the reagents impregnated in zone 56 to form signal generating products that are carried further to be caught at detection zone 55. Detection zone 55 typically comprises a region T where a member of second specific binding pairs, different from the first binding specific pair, is immobilized to the strip for capturing the analyte-label pair thereby producing a signal. Detection zone 55 may further include a control zone C to indicate that the test on the test has performed correctly. It will be realized that FIG. 7 is given by way of illustration only and that other test strips of different structures may be used without departing from the scope of the present invention.

It will be appreciated by persons skilled in the art that the present invention is not limited to what has been particularly shown and described hereinabove. Rather the scope of the present invention is defined only by the claims which follow.

The invention claimed is:

1. A diagnostic device for performing a diagnostic blood test of a subject, the device comprising a tubular body mountable on the subject's fingertip, wherein said tubular body comprises:
   an open end adapted to receive the subject's fingertip;
   a transparent window in said tubular body;
   a puncturing unit attached to said tubular body, the puncturing unit comprising a retractable lancing element for producing a blood sample from the subject's fingertip; and
   at least one diagnostic strip impregnated with assay specific reagents positioned inside said tubular body, the diagnostic strip comprising a sample receiving zone and a detection zone where a visible signal indicative of test results is formed, the diagnostic strip is positioned inside said tubular body such that said sample receiving zone is in fluid communication with the blood sample produced by said puncturing unit and said detection zone is visible through said transparent window.

2. The diagnostic device of claim 1 wherein said diagnostic strip is adapted for a lateral flow assay of a whole blood sample.

3. The diagnostic device of claim 2 wherein said assay is an immunoassay, an enzymatic assay, a biochemical assay or a chemical assay.

4. The diagnostic device of claim 2 wherein said assay is a positive/negative assay.

5. The diagnostic device of claim 1 wherein said diagnostic strip is configured for detecting the presence and/or concentration of an analyte in said blood sample.

6. The diagnostic device of claim 5 wherein the assay specific reagents include one or more reagents disposed along the diagnostic strip, said reagents are selected to provide a visible signal when said analyte is present in said sample.

7. The diagnostic device of claim 6 wherein said analyte is a blood borne pathogen.

8. The diagnostic device of claim 1 wherein said diagnostic strip comprises a whole blood separation zone for entrapping and retaining red blood cells.

9. The diagnostic device of claim 1 wherein said diagnostic strip comprises a reaction zone interposed between said sample receiving zone and said detection zone.

10. The diagnostic device of claim 1 further comprising a reservoir of a releasable reagent solution adapted to release the reagent solution to facilitate running the diagnostic test.

11. The diagnostic device according to claim 10 wherein said reservoir of the releasable reagent solution comprises a blister made of liquid impermeable film encapsulating said reagent solution.

12. The diagnostic device of claim 1 further comprising a safety means to prevent premature activation of the puncturing unit.

13. The diagnostic device of claim 1 wherein the retractable lancing element is a solid pointed element and wherein the blood sample is drawn away from the retractable lancing element into the diagnostic strip.

14. The diagnostic device of claim 1 wherein the retractable lancing element is configured to penetrate through said tubular body.

15. The diagnostic device of claim 1 wherein the retractable lancing element is configured to penetrate through a blood sample absorbent member in fluid communication with the detection zone of said diagnostic strip.

16. The diagnostic device of claim 1 wherein the tubular body is made of a plastic material.

17. The diagnostic device of claim 1 wherein the tubular body comprises means to limit the extent of penetration of the finger into said tubular body such that in use the subject's fingertip is positioned over a sample absorbent member in fluidic connection with the detection zone of the diagnostic strip.

18. A method for conducting a diagnostic blood test of a subject comprising:
   providing the diagnostic device of claim 1;
   mounting said diagnostic device on a fingertip of said subject;
   activating the puncturing unit to puncture said subject's fingertip to produce a blood sample;
   allowing the blood sample to be drawn from the subject's fingertip into the diagnostic strip; and
   detecting appearance of a signal in the detection zone of said diagnostic strip through the transparent window.

19. The method of claim 18, further comprising a step of puncturing a reservoir of a releasable reagent solution to be drawn into said diagnostic strip.

* * * * *